United States Patent [19]

Duncan

[11] Patent Number: 5,620,471
[45] Date of Patent: Apr. 15, 1997

[54] SYSTEM AND METHOD FOR DISCRIMINATING BETWEEN ATRIAL AND VENTRICULAR ARRHYTHMIAS AND FOR APPLYING CARDIAC THERAPY THEREFOR

[75] Inventor: James L. Duncan, Alpharetta, Ga.

[73] Assignee: Pacesetter, Inc., Sylmar, Calif.

[21] Appl. No.: 491,560

[22] Filed: Jun. 16, 1995

[51] Int. Cl.$^6$ .............................. A61N 1/36; A61N 1/362; A61N 1/365; A61N 1/368

[52] U.S. Cl. .................................. 607/14; 607/9; 607/15

[58] Field of Search ..................................... 607/9, 14, 15

[56] References Cited

U.S. PATENT DOCUMENTS

| | | | |
|---|---|---|---|
| 4,280,502 | 7/1981 | Baker, Jr. et al. | 128/419 PG |
| 4,312,356 | 1/1982 | Sowton et al. | 128/419 PG |
| 4,384,585 | 5/1983 | Zipes | 128/419 D |
| 4,390,021 | 6/1983 | Spurrell et al. | 128/419 PG |
| 4,398,536 | 8/1983 | Nappholz et al. | 128/419 PG |
| 4,406,287 | 9/1983 | Nappholz et al. | 128/419 PG |
| 4,408,606 | 10/1983 | Spurrell et al. | 128/419 PG |
| 4,427,011 | 1/1984 | Spurrell et al. | 128/419 PG |
| 4,432,375 | 2/1984 | Angel et al. | 128/419 D |
| 4,473,078 | 9/1984 | Angel | 128/419 D |
| 4,552,154 | 11/1985 | Hartlaub | 128/702 |
| 4,587,970 | 5/1986 | Holley et al. | 128/419 PG |
| 4,625,730 | 12/1986 | Fountain et al. | 128/419 D |
| 4,726,380 | 2/1988 | Vollmann et al. | 128/419 PG |
| 4,787,389 | 11/1988 | Tarjan | 128/419 PG |
| 4,790,317 | 12/1988 | Davies | 128/419 D |
| 4,796,620 | 1/1989 | Imran | 128/706 |
| 4,821,723 | 4/1989 | Baker, Jr. et al. | 128/419 D |
| 4,827,936 | 5/1989 | Pless et al. | 128/419 D |
| 4,830,006 | 5/1989 | Haluska et al. | 128/419 PG |
| 4,860,749 | 8/1989 | Lehmann | 607/14 |
| 4,869,252 | 9/1989 | Gilli | 128/419 PG |
| 4,872,459 | 10/1989 | Pless et al. | 128/419 PG |
| 4,875,483 | 10/1989 | Vollmann et al. | 128/419 PG |
| 4,895,151 | 1/1990 | Grevis et al. | 128/419 PG |
| 4,949,719 | 8/1990 | Pless et al. | 128/419 D |
| 4,989,602 | 2/1991 | Sholder et al. | 128/419 D |
| 4,998,974 | 3/1991 | Aker | 128/419 PG |
| 5,007,422 | 4/1991 | Pless et al. | 128/419 D |
| 5,014,697 | 5/1991 | Pless et al. | 128/419 D |
| 5,048,521 | 9/1991 | Pless et al. | 607/9 |
| 5,063,928 | 11/1991 | Grevis et al. | 128/419 D |
| 5,083,562 | 1/1992 | de Coriolis et al. | 128/419 D |
| 5,086,772 | 2/1992 | Larnard et al. | 128/419 D |
| 5,107,850 | 4/1992 | Olive | 128/705 |
| 5,205,283 | 4/1993 | Olson | 607/14 |
| 5,350,406 | 9/1994 | Nitzsche et al. | 607/14 |
| 5,411,530 | 5/1995 | Akhtar | 607/14 |

OTHER PUBLICATIONS

Echt, Debra S. et al., "Implantation and Intraoperative Assessment of Antitachycardia Devices," *Electrical Therapy of Tachyarrhyhmias*, Section III, Chapter 24, pp. 489–515, (Date Unknown).

Begemann, M.J.S. et al., "The Influence of Test Window Width on Atrial Rhythm Classification in Dual Chamber Pacemakers," *PACE*, vol. 15, pp. 2158–2163 (1992).

Saoudi, Nadir et al., "Stability of the Atrioventricular Relationship During Sustained Ventricular Tachycardias: A Clue for an Automatic Atrial Arrhythmias Recognition Algorithm," Abstract, p. 230 (Date Unknown).

(List continued on next page.)

*Primary Examiner*—George Manuel
*Assistant Examiner*—Carl H. Layno
*Attorney, Agent, or Firm*—Harold C. Schloss

[57] ABSTRACT

Improved methods and apparatus are provided for applying atrial and ventricular therapies to the heart of a patient using an implanted cardiac stimulating device. Atrial and ventricular heart rates are monitored and analyzed to determine whether the patient is suffering from an atrial or ventricular arrhythmia and to determine what type of therapy is appropriate to apply to the heart. Atrial and ventricular heart rates are compared to determine if the ventricular heart rate exceeds the atrial heart rate and to determine whether the ventricular heart Fate is stable. An early atrial stimulation pulse can also be applied to determine whether the ventricular heart rate follows the atrial heart rate. Atrial and ventricular therapies are applied to the heart based on these determinations.

26 Claims, 1 Drawing Sheet

OTHER PUBLICATIONS

Saoudi, Nadir et al., "Stability of Atrioventricular Relationship During Sustained Ventricular Tachycardia: A Clue for Automatic Atrial Arrhythmia Recognition," *CIRC Suppl. 1, 1992*; 86:I-58 (abstract 230) (Presented at 65th Scientific Sessions of the American Health Association, New Orleans, LA, Nov. 16-20, 1992.

Brugada, Pedro et al., "Optimal Methods to Assess PR and RR Stability for Automatic Recognition of Ventricular and Supraventricular Tachycardia," Abstract, p. 514, (Apr.).

Brugada, Pedro et al., "Methods to Assess PR and RR Stability for Automatic Recognition of Ventricular and Supraventricular Tachycardia," *PACE*, 15:514 (abstract 39) (Presented at the 13th Annual Scientific Session of the North American Society of Pacing and Electrophysiology, May 14-16, 1992, Chicago, Illinois).

SYSTEM AND METHOD FOR DISCRIMINATING BETWEEN ATRIAL AND VENTRICULAR ARRHYTHMIAS AND FOR APPLYING CARDIAC THERAPY THEREFOR

FIELD OF THE INVENTION

This invention relates to implantable cardiac stimulating devices which provide antiarrhythmia therapies to the heart (e.g., antitachycardia, cardioversion, and defibrillation), and more particularly to an improved method and system for discriminating between atrial and ventricular arrhythmias by analyzing the atrial and ventricular heart rates, and depending on such analysis, applying cardiac therapy in the appropriate chamber of the heart.

BACKGROUND OF THE INVENTION

Cardiac stimulating devices such as pacemakers and cardioverter-defibrillators are well known. A variety of devices are presently available that apply electrical pulses to a patient's heart in order to maintain a healthy heart rhythm. The simplest cardiac stimulating devices apply pacing pulses to the patient's heart at regular predetermined intervals. More sophisticated devices monitor the various heartbeat signals within a patient's heart so that the strength and timing of the electrical pulses applied to the heart can be specifically tailored to the patient's varying needs.

Cardiac stimulating devices contain detection circuitry to sense the patient's internal heartbeat signals via leads connected to the heart. For example, a bipolar lead connected to the patient's ventricle can be used to sense the patient's ventricular heart rate. By analyzing the rate and the stability of the ventricular heartbeat signal, some conventional cardiac stimulating devices are capable of determining whether the patient is suffering from an arrhythmia such as ventricular tachycardia (a condition in which the heart beats too quickly) or fibrillation (a condition in which the heart quivers chaotically).

Cardiac stimulating devices typically differ in the type of stimulation therapy that may be delivered to the patient's heart in response to a detected arrhythmia.

Antitachycardia pacemakers, for example, attempt to terminate detected ventricular tachycardia episodes by applying one or more bursts of fairly weak antitachycardia stimulation pulses to the patient's heart. More sophisticated devices contain cardioversion circuitry, which allows synchronous, higher energy cardioversion stimulation pulses (e.g., 0.5–5 J) to be used to terminate the arrhythmias. Cardiac stimulating devices with defibrillation capabilities can apply higher energy electrical stimulation pulses (e.g., 20–40 J). The various antitachycardia, cardioversion, and defibrillation stimulation pulses that are applied to the heart are all known as "cardiac stimulation therapies."

Typically, the various cardiac therapies are applied to the heart in a tiered fashion. Initial attempts to terminate an arrhythmia use the least aggressive methods such as applying bursts of antitachycardia pulses to the heart. If this fails to terminate the arrhythmia or if the arrhythmia accelerates in rate, a cardioversion shock, or ultimately a defibrillation shock may be applied.

In order to determine whether a patient is suffering from an episode of tachycardia that should be terminated by the application of a suitable therapy, cardiac stimulating devices typically measure the rate of a patient's ventricular heartbeat and monitor its stability. The stability (or regularity of the timing) of a patient's heartbeat from beat to beat is indicative of the patient's cardiac condition, because, as is well known, a normal human heartbeat is somewhat unstable, whereas cardiac arrhythmias—such as tachycardia episodes—are often stable. One of the reasons that many ventricular tachycardia episodes are stable is that they are sometimes caused by electrical heartbeat signals that have recirculated within the heart by a feedback pathway. A tachycardia episode that is caused by the feedback of heartbeat signals tends to be stable. Various algorithms have been developed for determining whether a patient's heartbeat should be classified as "stable". For example, the period of the most recently measured ventricular beat can be compared to the immediately preceding beat, or can be compared to a running average of recent heart beat periods.

If the ventricular heart rate exceeds a predetermined ventricular tachycardia threshold rate (e.g., 150 beats per minute "bpm"), and if the beats are determined to be stable, then appropriate ventricular therapy can be applied to the patient's heart. Although this technique is generally successful for terminating many potentially life-threatening tachycardias, there are some circumstances in which a more sophisticated approach would be preferred.

For example, occasionally a patient's ventricular heartbeat may exceed a predetermined ventricular tachycardia threshold and be relatively stable—normally an indication that ventricular therapy should be applied. It may be, however, that the elevated ventricular heart rate is due to an atrial arrhythmia that has produced electrical signals that have propagated to the ventricle. Atrial arrhythmias are undesirable, but are typically not life-threatening because the ventricles of the heart can continue to effectively pump blood even if the atrial heart chambers beat arrhythmically.

If a patient suffers from an atrial arrhythmia that causes a corresponding ventricular arrhythmia, applying ventricular electrical pulses to the patient's heart will usually be ineffective at terminating the arrhythmia episode. Applying ventricular therapy to the patient's heart in these circumstances may actually be harmful, because the ventricular electrical pulses may initiate a ventricular tachycardia episode or induce fibrillation.

Further, using conventional criteria for detecting ventricular antiarrhythmias, therapies are typically only applied if the ventricular heartbeat is found to be relatively stable using a stability analysis algorithm.

However, occasionally a ventricular arrhythmia may occur that is not sufficiently stable to be confirmed as a ventricular episode using conventional stability algorithms. Some arrhythmia episodes in which ventricular therapy would be appropriate are therefore not treated. These episodes could, however, be detected if atrial and ventricular heartbeat signals were analyzed properly.

What is needed, therefore, is a cardiac stimulating device that does not apply ventricular therapy to a patient's heart if the ventricular heart arrhythmia is due to an atrial arrhythmia condition, but which applies ventricular therapy when an analysis of the patient's ventricular and atrial heart rates indicates that it is proper to do so. If desired, the cardiac stimulating device could also apply atrial therapies to the patient's heart.

SUMMARY OF THE INVENTION

In accordance with the principles of the present invention, improved methods and apparatus are provided for applying atrial and ventricular therapies to the heart of a patient with an implanted cardiac stimulating device. The atrial and ventricular heartbeat signals of the patient's heart are monitored to determine whether atrial and ventricular therapies should be applied.

Compared with previously known approaches for applying cardiac therapies, which were both over- and under-inclusive, the present technique allows cardiac therapies to be applied more accurately by analyzing the measured atrial and ventricular heart rates.

For example, conventional cardiac stimulating devices do not apply ventricular therapy unless the ventricular heart rate is determined to be sufficiently stable.

With the present approach, ventricular therapy is applied, even if the ventricular heart rate is not stable, so long as the ventricular heart rate is determined to exceed the atrial heart rate.

Secondly, because of the possibility of polymorphic ventricular tachycardia (or a less organized ventricular tachycardia) being present along with a rapid atrial rate (such as atrial fibrillation), then ventricular therapy is applied, even if the ventricular heat rate is not stable, so long as a predetermined upper rate limit is attained.

Whenever the ventricular heart rate is less than the atrial rate, the present invention initiates a more detailed assessment of the arrhythmia. For example, if the ventricular rate equals the atrial rate, possible causes may be an accelerated sinus rhythm, a supraventricular tachycardia, or a ventricular tachycardia with 1:1 retrograde conduction. Both the supraventricular tachycardia and the ventricular tachycardia would be expected to have good stability.

Thus, the present invention activates a stability determination step whenever the atrial heart rate is greater than/or equal to the ventricular rate. The present invention then activates a tracking determination step, whenever the atrial heart rate is equal to the ventricular heart rate, to determine if tracking is occurring. Tracking is determined by generating a premature atrial stimulation pulse and verifying that the ventricular channel has reset. The combination of these three determinations (stability, rate and tracking) enables the present invention to distinguish between atrial and ventricular arrhythmias.

For example, if the heart rate is very stable, and the atrial heart rate exceeds the ventricular heart rate (thereby indicating no tracking), then a ventricular tachycardia is presumed and ventricular therapy is applied.

If the ventricular heart rate is stable and the ventricular heart rate equals the atrial heart rate, then appropriate atrial therapy can be applied, so long as ventricular beats are tracking the atrial beats.

If, on the other hand, the ventricular heart rate is stable and the ventricular heart rate equals the atrial heart rate, and the ventricular channel cannot be reset, then ventricular tachycardia is presumed and ventricular therapy is applied.

Atrial therapy can also be applied if the ventricular heart rate is not stable (initially indicating that the rhythm may be of natural origin) but further testing indicates that the atrial heart rate exceeds the ventricular heart rate, thereby indicating that the arrhythmia is originating in the atrium.

BRIEF DESCRIPTION OF THE DRAWINGS

The above and other advantages of the invention will be apparent upon consideration of the following detailed description, taken in conjunction with the accompanying drawings, in which like reference numerals refer to like parts throughout, and in which.

DETAILED DESCRIPTION OF THE PREFERRED EMBODIMENTS

Previously-known cardiac stimulating devices have both over- and under-applied ventricular therapies to patient's hearts. For example, ventricular therapies have been over-applied when measured ventricular heart rates have exceeded a predetermined threshold rate and have been determined to be stable. In these circumstances, conventional cardiac stimulating devices have uniformly applied ventricular therapies. However, this approach for determining whether ventricular therapy is warranted is over-inclusive, because it does not take into account the possibility that the ventricular arrhythmia may be due to an atrial arrhythmia. If the ventricular arrhythmia is caused by an underlying atrial arrhythmia, ventricular therapies will usually be ineffective. Further, if such ventricular therapies are applied, they may adversely affect the patient's condition, for example, by precipitating a more serious cardiac event such as a ventricular fibrillation.

Previously-known cardiac stimulating devices have also under-applied ventricular therapies, because the conventional approach of applying therapy only if the ventricular beat satisfies various stability criteria occasionally fails to identify certain ventricular arrhythmias. Various algorithms for determining if the ventricular beat is stable have been developed and are well known. Although such algorithms are generally satisfactory for determining whether a ventricular beat is stable and thus corresponds to an arrhythmia, some arrhythmias remain undetected.

Figure 1:
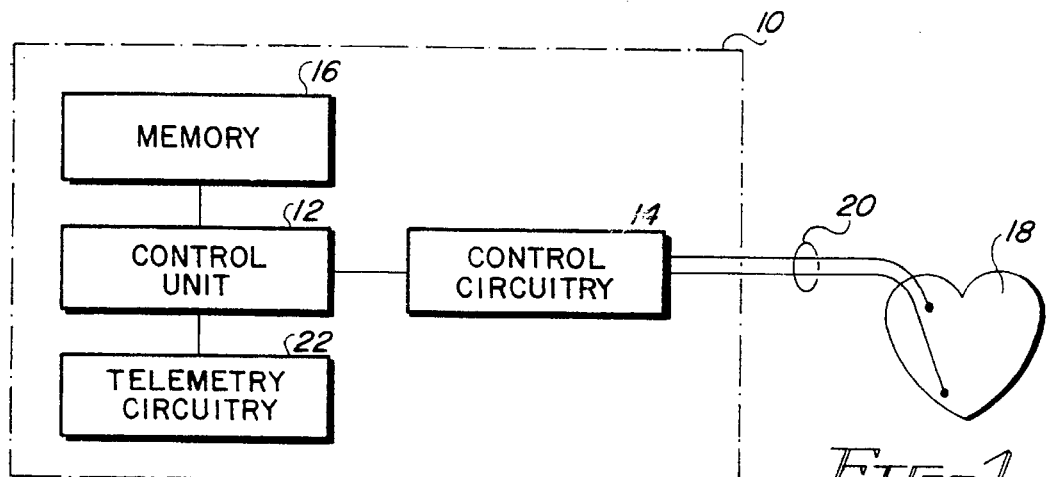
FIG. 1 is a simplified schematic diagram of the implantable cardiac stimulating device of the present invention shown connected to a patient's heart by an illustrative pair of leads.

The shortcomings of conventional cardiac stimulating devices are overcome by the cardiac stimulating device of the present invention. A cardiac stimulating device 10 constructed in accordance with the invention is shown schematically in FIG. 1. The operation of the cardiac stimulating device is controlled by a control unit 12 and control circuitry 14. The control unit 12, which is preferably microprocessor-based, executes instructions stored in memory 16. The control circuitry 14 preferably contains suitable circuitry for sensing the patient's heartbeat signals. The control circuitry 14 also preferably contains suitable circuitry for generating appropriate electrical pulses to be applied to the patient's heart 18. The control circuitry 14 is connected to the patient's heart 18 via leads 20.

Preferably, the arrangement of the leads 20 allows both atrial and ventricular heartbeat signals to be sensed. Any suitable lead configuration can be used. For example, two bipolar leads (one connected to the atrium and one to the ventricle) can be used to sense both atrial and ventricular heart activity and to apply appropriate electrical pulses to the heart. If desired, the leads 20 can incorporate one or more patches or other suitable electrodes. Preferably, the leads 20 are suitable for allowing the cardiac stimulating device 10 to deliver cardioversion and defibrillation pulses to the heart.

Some of the parameters that affect the operation of the cardiac stimulating device 10 are preferably selected by a physician. The physician programs parameters into the cardiac stimulating device 10 using a conventional programmer (not shown). The parameters selected by the physician can be loaded into the cardiac stimulating device 10 using conventional telemetry. For this purpose, the cardiac stimulating device 10 preferably has telemetry circuitry 22 for receiving the programming data.

Although the cardiac stimulating device 10 preferably has pacemaker antitachycardia capabilities as well as cardioversion and defibrillation capabilities, the features of the present invention are equally applicable to a number of various cardiac stimulating device configurations. For example, the cardiac stimulating device 10 can provide only the functions of a pacemaker with an antitachycardia capability (such as the ability to apply a burst of pulses to a patient's ventricle) or the functions of a cardioverter-defibrillator with no pacemaker antitachycardia functions.

Figure 2:
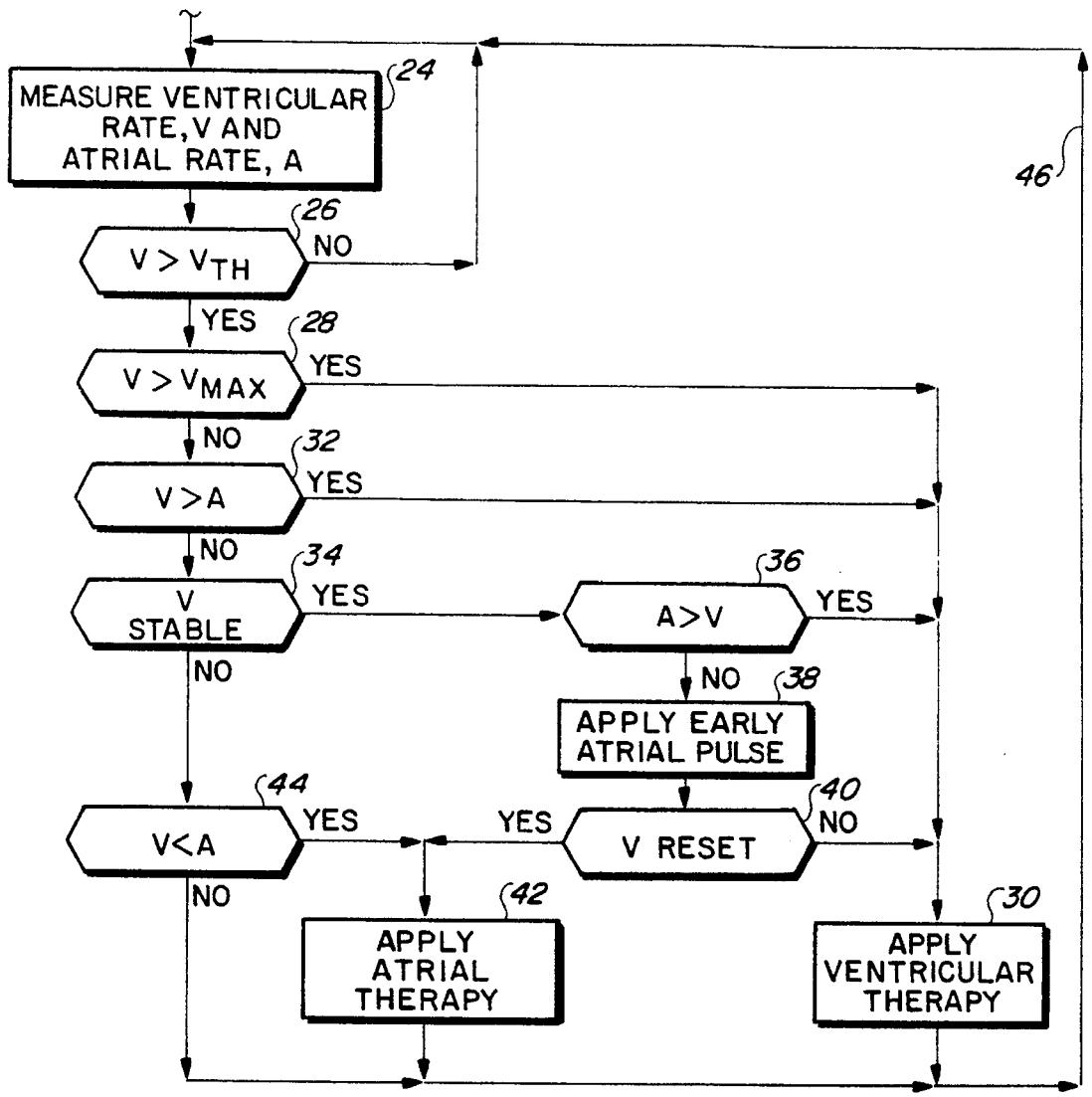
FIG. 2 is a flow chart diagram of certain steps performed by the cardiac stimulating device of FIG. 1.

The cardiac stimulating device 10 of the present invention allows cardiac therapies to be applied more effectively than has previously been possible, in part by monitoring both atrial and ventricular heartbeat signals and by comparing the respective atrial and ventricular heart rates. A number of the steps involved in determining the appropriate cardiac therapy to apply to a patient's heart are shown in FIG. 2.

The ventricular heart rate, V, and atrial heart rate, A, are measured by the cardiac stimulating device 10 (FIG. 1) at step 24. At test 26, the cardiac stimulating device 10 (FIG. 1) compares the measured ventricular heart rate, V, to a predetermined threshold value, $V_{TH}$ (e.g. 150 bpm), which has been determined to be a rate that corresponds to a value lower than the tachycardia rate for a particular patient. The predetermined threshold value, $V_{TH}$, may be derived in any of a variety of methods, for example, $V_{TH}$, could be based on the last cycle length, or the average of several cycle lengths, etc.

If the measured ventricular heart rate, V, does not exceed the predetermined ventricular tachycardia threshold, $V_{TH}$, then control loops back to step 24. During the process of looping back, the various other functions of the cardiac stimulating device 10 (FIG. 1) that are necessary for the operation of the device can be performed.

If the measured ventricular heart rate, V, exceeds the predetermined ventricular threshold, $V_{TH}$, then the cardiac stimulating device 10 (FIG. 1) determines whether the ventricular heart rate, V, exceeds a higher threshold, $V_{MAX}$ (e.g., 220 bpm), at test 28. This optional step allows ventricular therapy to be applied to the patient's heart at step 30 in the event that the ventricular heart rate exceeds a relatively high rate. When this rate is exceeded, it is likely that the patient is suffering from a polymorphic ventricular tachycardia, which would benefit from the application of ventricular therapy.

If the measured ventricular heart rate, V, does not exceed the threshold, $V_{MAX}$, then at test 32 it is determined whether or not the ventricular heart rate, V, exceeds the atrial heart rate, A. If the ventricular heart rate, V, exceeds the atrial heart rate, A, the heart is experiencing a ventricular arrhythmia that is treated by applying ventricular therapy at step 30. If the ventricular heart rate does not exceed the atrial heart rate then suitable conventional stability criteria are applied at test 34 to determine whether or not the ventricular heart rate, V, is stable.

If the ventricular heart rate is stable, then at test 36 it is further determined whether or not the atrial heart rate, A, exceeds the ventricular heart rate, V. If the atrial heart rate, A, exceeds the ventricular heart rate, V, then ventricular therapy is applied at step 30. If the atrial heart rate, A, does not exceed the ventricular heart rate, V, at test 36, then the atrial and ventricular heart rates are equal. In this situation, it is desirable to differentiate between those ventricular arrhythmias that are directly the result of atrial arrhythmias and those that are independent ventricular arrhythmias. Thus, at step 38, an atrial pacing pulse is preferably applied that is slightly advanced relative to the measured atrial rhythm. For example, if the measured atrial heart rate is 180 bpm, then an atrial pacing pulse can be applied at a rate of 200 bpm. If it is determined at test 40 that the ventricular pulse rate is unaffected by the early pulse, then ventricular therapy is applied at step 30. If at test 40 it is determined that the early pulse results in a resetting of the ventricular heart rate (i.e., the ventricular pulse follows the early atrial stimulation pulse), then the ventricular arrhythmia is the result of the atrial arrhythmia and no ventricular therapy is applied. This is in contrast to previously known cardiac stimulating devices, in which all stable ventricular beats exceeding the ventricular tachycardia threshold resulted in the application of ventricular therapy, regardless of whether the cause of the ventricular arrhythmia was due to an atrial arrhythmia—a condition best not treated with ventricular therapy.

If the ventricular heart rate is found to be reset at test 40, appropriate atrial therapy (such as bursts of atrial stimulation pulses, etc.) may be applied to the patient's heart at step 42. The application of atrial therapy at step 42 is optional and the decision of whether to invoke atrial therapy is preferably made by the physician. For example, if the physician determines that a patient does not suffer from atrial arrhythmias, then atrial therapy will not be applied, regardless of the results of test 40.

If at test 34 it was determined that the ventricular heart rate was not stable, then at test 44 the cardiac stimulating device 10 (FIG. 1) determines whether the atrial heart rate, A, exceeds the ventricular heart rate, V. If it is determined that the atrial heart rate, A, exceeds the ventricular heart rate, V, at test 44, then optional atrial therapy may be applied at step 42. If the atrial heart rate is not found to exceed the ventricular heart rate at test 44, then the atrial and ventricular heart rates are equal, which indicates that the patient is probably exhibiting a normal—albeit elevated—sinus rhythm. Thus, no therapies are applied if the outcome of test 44 is negative. Following a negative outcome of test 44 and following the application of atrial and ventricular therapies at steps 42 and 30, control returns to step 24 via loop 46.

One skilled in the art will appreciate that the present invention can be practiced by other than the described embodiments, which are presented for the purposes of illustration and not of limitation, and the present invention is limited only by the claims that follow.

What is claimed is:

1. An implantable cardiac stimulating device for monitoring and stimulating the heart of a patient, the cardiac stimulating device comprising:

means for measuring intrinsic atrial and ventricular heart rates;

rate determining means for determining whether the ventricular heart rate is less than, equal to or exceeds the atrial heart rate;

ventricular stimulation means for applying ventricular stimulation therapy to the heart when the rate determining means determines that the ventricular heart rate exceeds the atrial heart rate;

stability determining means for determining whether the ventricular heart rate is stable, wherein a stable ventricular heart rate provides an indication that the rhythm is a tachycardia and an unstable ventricular heart rate provides an indication that the rhythm requires further testing to determine if it is of natural origin;

atrial pulse generating means for applying an atrial stimulation pulse to the heart at a rate slightly faster than the measured intrinsic atrial heart rate;

reset determining means for determining whether the ventricular heart rate is reset by the atrial stimulation pulse, whereby the resetting of the ventricular heart rate provides an indication that the ventricle is tracking the atrium; and atrial stimulation means for applying atrial stimulation therapy to the heart when:
 the stability determining means determines that the ventricular heart rate is stable;
 the rate determining means determines that the atrial heart rate is equal to the ventricular heart rate; and
 the reset determining means determines that the ventricular heart rate is reset by the atrial stimulation pulse, thereby indicating that the ventricle is tracking the atrium and an atrial arrhythmia is present.

2. An implantable cardiac stimulating device for monitoring and stimulating the heart of a patient, the cardiac stimulating device comprising:

means for measuring intrinsic atrial and ventricular heart rates;

rate determining means for determining whether the ventricular heart rate is less than, equal to or exceeds the atrial heart rate;

ventricular stimulation means for applying ventricular stimulation therapy to the heart when the rate determining means determines that the ventricular heart rate exceeds the atrial heart rate;

stability determining means for determining whether the ventricular heart rate is stable, wherein a stable ventricular heart rate provides an indication that the rhythm is a tachycardia and an unstable ventricular heart rate provides an indication that the rhythm requires further testing to determine if it is of natural origin; and atrial stimulation means for applying atrial stimulation therapy to the heart when:
 the stability determining means determines that the ventricular heart rate is not stable; and
 the rate determining means determines that the atrial heart rate exceeds the ventricular heart rate, thereby indicating an atrial arrhythmia is present.

3. The cardiac stimulating device defined in claim 2, further comprising:

atrial pulse generating means for applying an atrial stimulation pulse to the heart at a rate slightly faster than the measured intrinsic atrial heart rate; and reset determining means for determining whether the ventricular heart rate is reset by the atrial stimulation pulse, whereby the resetting of the ventricular heart rate provides an indication that the ventricle is tracking the atrium.

4. The cardiac stimulating device defined in claims 1 or 2, further comprising:

means for activating the stability determining means in response to the rate determining means determining that the ventricular heart rate does not exceed the atrial heart rate.

5. The cardiac stimulating device defined in claims 1 or 2, wherein the ventricular stimulation means further comprises means for applying ventricular stimulation therapy to the heart when:
 the stability determining means determines that the ventricular heart rate is stable;
 the rate determining means determines that the atrial heart rate is equal to the ventricular heart rate; and
 the reset determining means determines that the ventricular heart rate is not reset by the atrial stimulation pulse, thereby indicating that the ventricle is not tracking the atrium and a ventricular tachycardia exists.

6. The cardiac stimulating device defined in claims 1 or 2, wherein the ventricular stimulation means further comprises means for applying ventricular stimulation therapy to the heart when:
 the stability determining means determines that the ventricular heart rate is stable; and
 the rate determining means determines that the atrial heart rate exceeds the ventricular heart rate, thereby indicating a ventricular arrhythmia is present.

7. The cardiac stimulating device defined in claims 1 or 2, wherein the rate determining means further comprises:

means for determining whether the ventricular heart rate exceeds a first predetermined threshold ventricular heart rate; and means for determining whether the ventricular heart rate exceeds a second predetermined threshold ventricular heart rate that is greater than the first predetermined threshold ventricular heart rate;

wherein the ventricular stimulation means applies ventricular stimulation therapy when the ventricular heart rate exceeds the second predetermined threshold ventricular heart rate.

8. An implantable cardiac stimulating device for monitoring and stimulating the heart of a patient, the cardiac stimulating device comprising:

means for measuring intrinsic atrial and ventricular heart rate;

rate determining means for determining whether the atrial heart rate exceeds the ventricular heart rate; and stability determining means for determining whether the ventricular heart rate is stable;

means for applying ventricular stimulation therapy to the heart when:
 the stability determining means determines that the ventricular heart rate is stable; and
 the rate determining means determines that the atrial heart rate exceeds the ventricular heart rate;

atrial pulse generating means for applying an atrial pacing pulse to the heart at a rate slightly faster than the measured intrinsic atrial heart rate;

reset determining means for determining whether the ventricular heart rate is reset by the atrial stimulation pulse, whereby the resetting of the ventricular heart rate provides an indication that the ventricle is tracking the atrium; and means for applying atrial stimulation therapy to the heart when:
 the stability determining means determines that the ventricular heart rate is stable;
 the rate determining means determines that the atrial heart rate does not exceed the ventricular heart rate; and
 the reset determining means determines that the ventricular heart rate is reset by the atrial stimulation pulse, thereby indicating that the ventricle is tracking the atrium and an atrial arrhythmia is present.

9. An implantable cardiac stimulating device for monitoring and stimulating the heart of a patient, the cardiac stimulating device comprising means for measuring intrinsic atrial and ventricular heart rate;

rate determining means for determining whether the atrial heart rate exceeds the ventricular heart rate; and stability determining means for determining whether the ventricular heart rate is stable;

means for applying ventricular stimulation therapy to the heart when:
  the stability determining means determines that the ventricular heart rate is stable; and
  the rate determining means determines that the atrial heart rate exceeds the ventricular heart rate; and atrial stimulation means for applying atrial stimulation therapy to the heart when:
  the stability determining means determines that the ventricular heart rate is not stable; and
  the rate determining means determines that the atrial heart rate exceeds the ventricular heart rate, thereby providing an indication that an atrial arrhythmia is present.

10. The cardiac stimulating device defined in claim 8 or 9, further comprising:
  means for activating the stability determining means in response to the rate determining means determining that the atrial heart rate is greater than or equal to the ventricular heart rate.

11. The cardiac stimulating device defined in claims 8 or 9, wherein the ventricular stimulation means further comprises means for applying ventricular stimulation therapy to the heart when:
  the stability determining means determines that the ventricular heart rate is stable;
  the rate determining means determines that the atrial heart rate does not exceed the ventricular heart rate; and
  the reset determining means determines that the ventricular heart rate is not reset by the atrial stimulation pulse.

12. The cardiac stimulating device defined in claims 8 or 9, wherein the rate determining means further comprises:
  means for determining whether the ventricular heart rate exceeds a first predetermined threshold ventricular heart rate; and
  means for determining whether the ventricular heart rate exceeds a second predetermined threshold ventricular heart rate that is greater than the first predetermined threshold ventricular heart rate;
  wherein the ventricular stimulation means applies ventricular stimulation therapy whenever the rate determining means determines that the ventricular heart rate exceeds the second predetermined threshold ventricular heart rate.

13. The cardiac stimulating device defined in claims 8 or 9, wherein:
  the rate determining means further comprises means for determining whether the ventricular heart rate exceeds the atrial heart rate;
  the ventricular stimulation means applies ventricular stimulation therapy when the rate determining means determines that the ventricular heart rate exceeds the atrial heart rate.

14. A method for monitoring and stimulating the heart of a patient with an implantable cardiac stimulating device comprising the steps of:
  measuring an atrial heart rate and a ventricular heart rate;
  determining whether the ventricular heart rate exceeds the atrial heart rate;
  applying ventricular stimulation therapy to the heart when the ventricular heart rate exceeds the atrial heart rate;
  determining whether the ventricular heart rate is stable;
  determining whether the atrial heart rate exceeds the ventricular heart rate;
  applying an atrial pacing pulse to the heart at a rate slightly faster than the measured intrinsic atrial heart rate;
  determining whether the ventricular heart rate is reset by the atrial stimulation pulse; and
  applying atrial stimulation therapy to the heart when:
    the ventricular heart rate is stable;
    the atrial heart rate does not exceed the ventricular heart rate; and
    the ventricular heart rate is reset by the atrial stimulation pulse.

15. A method for monitoring and stimulating the heart of a patient with an implantable cardiac stimulating device comprising the steps of:
  measuring an atrial heart rate and a ventricular heart rate;
  determining whether the ventricular heart rate exceeds the atrial heart rate;
  applying ventricular stimulation therapy to the heart when the ventricular heart rate exceeds the atrial heart rate;
  determining whether the ventricular heart rate is stable;
  determining whether the atrial heart rate exceeds the ventricular heart rate; and
  applying atrial stimulation therapy to the heart when:
    the ventricular heart rate is not stable; and
    the atrial heart rate exceeds the ventricular heart rate.

16. The method defined in claims 14 or 15, further comprising the step of:
  triggering the stability determining step whenever the ventricular heart rate does not exceed the atrial heart rate.

17. The method defined in claims 14 or 15, wherein the ventricular stimulation therapy applying step applies therapy to the heart when:
  the ventricular heart rate is stable;
  the atrial heart rate does not exceed the ventricular heart rate; and
  the ventricular heart rate is not reset by the atrial stimulation pulse.

18. The method defined in claims 14 or 15, further comprising the step of supplying ventricular stimulation therapy to the heart when:
  the ventricular heart rate is stable; and
  the atrial heart rate exceeds the ventricular heart rate.

19. The method defined in claims 14 or 15, further comprising the step of:
  determining whether the ventricular heart rate exceeds a first predetermined threshold ventricular heart rate.

20. The method defined in claim 19, further comprising the step of:
  determining whether the ventricular heart rate exceeds a second predetermined threshold ventricular heart rate that is greater than the first predetermined threshold ventricular heart rate;
  wherein the ventricular stimulation therapy is applied to the heart when the ventricular heart rate exceeds the second predetermined threshold ventricular heart rate.

21. A method for monitoring and stimulating the heart of a patient with an implantable cardiac stimulating device comprising the steps of:

measuring an atrial heart rate and a ventricular heart rate;

determining whether the ventricular heart rate is stable;

determining whether the atrial heart rate exceeds the ventricular heart rate;

applying ventricular stimulation therapy to the heart when the ventricular heart rate is stable and the atrial heart rate exceeds the ventricular heart rate;

applying an atrial pacing pulse to the heart;

determining whether the ventricular heart rate is reset by the atrial stimulation pulse; and applying atrial stimulation therapy to the heart when:

the ventricular heart rate is stable;

the atrial heart rate is equal to the ventricular heart rate; and the ventricular heart rate is reset by the atrial stimulation pulse.

22. A method for monitoring and stimulating the heart of a patient with an implantable cardiac stimulating device comprising the steps of:

measuring an atrial heart rate and a ventricular heart rate;

determining whether the ventricular heart rate is stable;

determining whether the atrial heart rate exceeds the ventricular heart rate;

applying ventricular stimulation therapy to the heart when the ventricular heart rat is stable and the atrial heart rate exceeds the ventricular heart rate; and applying atrial stimulation therapy to the heart when:

the ventricular heart rate is not stable; and the atrial heart rate exceeds the ventricular heart rate.

23. The method defined in claims 21 or 22, further comprising the steps of:

determining whether the ventricular heart rate exceeds a first predetermined threshold ventricular heart rate;

determining whether the ventricular heart rate exceeds a second predetermined threshold ventricular heart rate that is greater than the first predetermined threshold ventricular heart rate; and applying ventricular stimulation therapy to the heart when the ventricular heart rate exceeds the second predetermined threshold ventricular heart rate.

24. The method defined in claims 21 or 22, further comprising the step of:

determining whether the ventricular heart rate exceeds the atrial heart rate; and triggering the stability determining step whenever the ventricular heart rate does not exceed the atrial heart rate.

25. The method defined in claims 21 or 22, further comprising the steps of:

applying an atrial stimulation pulse to the heart; and determining whether the ventricular heart rate is reset by the atrial stimulation pulse.

26. The method defined in claim 25, further comprising the step of applying ventricular stimulation therapy to the heart when:

the ventricular heart rate is stable;

the atrial heart rate is equal to the ventricular heart rate; and the ventricular heart rate is not reset by the atrial stimulation pulse.

* * * * *